(12) United States Patent
Sinclair et al.

(10) Patent No.: US 9,952,154 B2
(45) Date of Patent: Apr. 24, 2018

(54) SEPARATED PARALLEL BEAM GENERATION FOR ATOM INTERFEROMETRY

(71) Applicant: The Charles Stark Draper Laboratory, Inc., Cambridge, MA (US)

(72) Inventors: Matthew A. Sinclair, Stoneham, MA (US); Adam Kelsey, Newton, MA (US); Richard E. Stoner, Framingham, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 15/402,399

(22) Filed: Jan. 10, 2017

(65) Prior Publication Data

US 2017/0370840 A1 Dec. 28, 2017

Related U.S. Application Data

(60) Provisional application No. 62/353,415, filed on Jun. 22, 2016.

(51) Int. Cl.
*G01B 9/02* (2006.01)
*G21K 1/00* (2006.01)
*G01N 21/64* (2006.01)

(52) U.S. Cl.
CPC ..... *G01N 21/6404* (2013.01); *G01B 9/02015* (2013.01); *G01N 21/645* (2013.01); *G21K 1/006* (2013.01); *G01B 2290/55* (2013.01); *G01N 2021/6463* (2013.01); *G01N 2201/06113* (2013.01)

(58) Field of Classification Search
USPC ............... 250/251, 269.1, 526; 356/451
See application file for complete search history.

(56) References Cited

U.S. PATENT DOCUMENTS

| | | | | |
|---|---|---|---|---|
| 5,351,122 A | * | 9/1994 | Niebauer | G01P 15/093 356/28.5 |
| 6,891,623 B1 | * | 5/2005 | Baudon | B82Y 10/00 356/450 |
| 9,018,579 B2 | * | 4/2015 | Kasevich | G01B 9/02041 250/251 |

(Continued)

OTHER PUBLICATIONS

Barrett et al., "Mobile and remote inertial sensing with atom interferometers," *Societá Italiana di Fisica*, Aug. 13, 2014, 63 pages.

(Continued)

*Primary Examiner* — Bernard Souw
(74) *Attorney, Agent, or Firm* — Sunstein Kann Murphy & Timbers LLP (57) ABSTRACT

An atomic interferometer and methods for measuring phase shifts in interference fringes using the same. The atomic interferometer has a laser beam traversing an ensemble of atoms along a first path and an optical components train with at least one alignment-insensitive beam routing element configured to reflect the laser beam along a second path that is anti-parallel with respect to the first laser beam path. Any excursion from parallelism of the second beam path with respect to the first is rigorously independent of variation of the first laser beam path in yaw parallel to an underlying plane.

11 Claims, 9 Drawing Sheets

(56) References Cited

U.S. PATENT DOCUMENTS

| | | | | |
|---|---|---|---|---|
| 9,019,506 B1* | 4/2015 | Black | ............. | G01B 9/02 |
| | | | | 356/450 |
| 9,030,655 B2* | 5/2015 | Strabley | ............. | G01P 21/00 |
| | | | | 356/72 |
| 2011/0101972 A1* | 5/2011 | Narducci | ............. | G01R 33/022 |
| | | | | 324/244 |
| 2014/0022534 A1* | 1/2014 | Strabley | ............. | G01P 21/00 |
| | | | | 356/72 |
| 2014/0190254 A1* | 7/2014 | Bouyer | ............. | G01V 7/14 |
| | | | | 73/382 G |

OTHER PUBLICATIONS

Carter et al., "Risley Prisms: 125 Years of New Applications," *Eos*, vol. 87, No. 28, pp. 273, 276, Jul. 2006.
Cronin et al., "Optics and interferometry with atoms and molecules," *Reviews of Modern Physics*, vol. 81, No. 3, pp. 1051-1129, Jul.-Sep. 2009.
Erickson C.J., "Construction of a Calcium Matter-Wave Interferometer," *Brigham Young University*, Thesis, 96, pages, Nov. 2007.
Friebe et al., "Absolute frequency measurement of the magnesium intercombination transition $^1S_0 \rightarrow {}^3P_1$," arXiv:0711.4926v1, Nov. 2007, 8 pages [physics.atom-ph].
McGuirk et al., "Sensitive Absolute Gravity Gradiometry Using Atom Interferometry," , arXiv:physics/0105088, May 2001, 25 pages [physics.atom-ph].
Jin Ho Kim, Authorized officer Korean Intellectual Property Office, International Search Report—Application No. PCT/US2017/035727, dated Sep. 4, 2017, 11 pages, together with the Written Opinion of the International Searching Authority.

* cited by examiner

SEPARATED PARALLEL BEAM GENERATION FOR ATOM INTERFEROMETRY

The present application claims priority from U.S. Provisional Application Ser. No. 62/353,415, filed Jun. 22, 2016, and incorporated herein by reference.

TECHNICAL FIELD

The present invention relates to atomic interferometry, and, more particularly, to optical configurations that enable unprecedented precision and stability of atomic interferometric measurements.

BACKGROUND ART

Atom interferometers use the wave character of atoms as a technique for precision measurements in geodesy, inertial navigation, time, and fundamental physics. Atom interferometry is typically performed by manipulating quantum objects, such as atoms, by applying one or more sequences of coherent beam splitting sequences. After being split into two parts by a coherent beam-splitting process, the atomic wavepackets move along two different paths for an interrogation time, during which the two atomic wavepackets accumulate different phases.

Some of the most precise measurements of physical quantities currently available derive from atomic interferometry. These include limits on composition-dependent gravitational forces (Einstein's principle of equivalence), measurements of the ratio $$\frac{\hbar}{m}$$

in an atom, and derivative determinations of the fine structure constant. Measurements of such exquisite precision require stability in the face of external factors such as temperature or pressure variations and other mechanical or optical perturbations.

Certain types of atom interferometers employ the use of multiple, spatially separated, parallel laser beams for producing the interferometer interaction. Maintaining parallel alignment of these laser beams is often critical for proper operation of the device, since loss of parallelism can result in sensors drift and/or loss of signal. Typical separated beam atom interferometer systems rely on mirrors, beam splitters, and retro-reflectors to implement parallel sets of laser beams. The alignment of these systems can be affected by any one of a number of different external factors, including temperature variation and system perturbation.

A comprehensive review of atomic interferometers may be found in Cronin, et al., "Optics and Interferometry with Atoms and Molecules," Rev. Mod. Phys., vol. 81, pp. 1051-129 (2009), which is incorporated herein by reference. A particular example is provided by Erickson, "Construction of a Calcium Matter-Wave Interferometer," Masters Dissertation, Brigham Young University (2007) (hereinafter, "Erickson"), which is incorporated herein by reference. Erickson points out that mechanical and thermal vibrations in the optics preceding the cavity are written onto the laser light as noise. (Erickson, p. 64) The remedy provided by Erickson is to place the optics inside a 1-inch thick aluminum enclosure. Beam steering, as shown in Erickson's FIG. 4.1, is achieved by means of prism reflectors and flat mirrors separately mounted on kinetic tilt mounts.

Configurations in which external factors may bear on the angle at which successive laser beams impinge on a probed atomic ensemble, such as a beam of thermal atoms, are prone to measurement perturbations and drift that may ultimately limit system sensitivity. Thus, a configuration that would, by its nature, cancel such perturbations and drift, is particularly valuable. Such a configuration is taught for the first time herein.

SUMMARY OF EMBODIMENTS OF THE INVENTION

In accordance with embodiments of the present invention, an atomic interferometer is provided that has an ensemble of atoms and a laser beam traversing the ensemble of atoms in a first laser beam path. An optical components train, comprising at least one alignment-insensitive beam routing element, is configured to reflect the laser beam along a second laser beam path that is anti-parallel with respect to the first laser beam path. The atomic interferometer also has an entirely refractive alignment element for steering the laser beam into the optical components train, and a detector configured to detect spontaneous fluorescence emitted by atoms within the ensemble of atoms after traversal of the first and second laser beam paths.

In accordance with certain other embodiments of the present invention, the ensemble of atoms may include a beam of atoms traversing a vacuum chamber, and the alignment-insensitive beam routing element may include at least one of a pentaprism pair, a pentamirror pair, a roof pentaprism pair, a roof pentamirror pair, a corner cube and a roof reflector. The alignment-insensitive beam routing element may be disposed within the vacuum chamber, and any angular perturbation of the first laser beam path external to the vacuum chamber may be common to the first laser beam path and the second laser beam path.

In accordance with a further aspect of the present invention, an atomic interferometer is provided that has an ensemble of atoms with a laser beam traversing the ensemble of atoms, and an optical component train, comprising at least one alignment-insensitive beam routing element, configured within the vacuum enclosure to reflect the laser beam along a second laser beam path that is anti-parallel with respect to the first laser beam path. The atomic interferometer also has an entirely refractive alignment element for steering the laser beam into the optical components train, and a detector configured to detect spontaneous fluorescence emitted by atoms within the ensemble of atoms after traversal of the first and second laser beam paths. Any excursion in yaw of the first laser beam path with respect to the ensemble of atoms is rigorously common mode to the first and second laser beam paths.

In alternate embodiments of the invention, the alignment-insensitive beam routing element may include at least one of a monolithically mounted pentaprism pair, a monolithically mounted pentamirror pair, and a roof reflector, and, more particularly, a matched pair of pentaprisms or pentamirrors. The atomic interferometer may also have at least a second alignment-insensitive beam routing element, configured within the vacuum enclosure to reflect the laser beam along a fourth laser beam path that is anti-parallel with respect to a third laser beam path.

In accordance with another aspect of the present invention, a method is provided for measuring relative phase shifts in interference fringes between populations of internal states of a quantum system. The method has steps of:

generating an ensemble of free atoms within a vacuum chamber;

coupling a laser beam so as to traverse the ensemble of atoms in a first laser beam path;

configuring at least one alignment-insensitive beam routing element within the vacuum enclosure to reflect the laser beam along a second laser beam path that is anti-parallel with respect to the first laser beam path;

aligning the first laser beam path with respect to the ensemble of atoms solely by refractive optics; and detecting spontaneous fluorescence emitted by atoms within the ensemble of atoms after traversal of the first and second laser beam paths.

In accordance with yet another embodiment of the invention, configuring the at least one alignment-insensitive beam routing element may include providing one or more of a monolithically mounted pentaprism pair, pentamirror pair and a roof reflector.

BRIEF DESCRIPTION OF THE DRAWINGS

The invention will be more fully understood by referring to the following Detailed Description of Specific Embodiments in conjunction with the Drawings. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

DETAILED DESCRIPTION OF SPECIFIC EMBODIMENTS

Definitions

The following terms shall be given the indicated meanings unless the context dictates otherwise.

As the term is used herein and in any appended claims, the term "quantum object" shall designate a physical system whose energy states are quantized, which is to say that the eigenstates of a Hamiltonian describing the system are discrete. Atoms and molecules are examples of quantum objects.

As the term is used herein and in any appended claims, the term "propagation axis" shall designate the axis that includes a ray that constitutes the centroid of directions characterizing momenta of particles in a beam.

The term "antiparallel," as referring to two beams, shall mean that the beams are substantially parallel but oriented in opposing directions.

The term "alignment-insensitive beam routing element" refers to an optical device or system wherein any excursion of the direction of a reflected beam relative to an incident beam is dominated by the manufacturing tolerance of the beam routing element and not by the orientation of the beam routing element relative to the beam.

The term "insensitive," as used herein in reference to an optic or set of optics, shall denote that the exit direction of an optical beam relative to a direction of incidence is less than two times the cumulative manufacturing tolerance of the optic or set of optics.

An "angle of incidence," and, synonymously, an "incident angle," shall denote the angle between an incident ray and a normal to the surface of an optic impinged upon by the ray. An "incident ray" shall refer to the Poynting vector or propagation axis 770 (shown in FIG. 7A) associated with an optical wave or optical beam 714 (shown in FIG. 7A).

The term "alignment optics," as used herein and in any appended claims, shall refer to any optical element, or set thereof, used to align an optical beam with respect to an ensemble of atoms and/or to compensate for tolerances of alignment-insensitive beam-routing elements.

The term "laser beam" shall refer to any optical output of a laser, irrespective of its degree of collimation.

A "matched pair" of optical elements shall refer to two of such elements that are selected for use in an optical system so that manufacturing errors are canceled, at least in part.

Optical Interferometers

Solely by way of heuristic introduction, the operation of optical interferometers is reviewed, as a paradigm of classical interference to which quantum interference in the operation of an atomic interferometer may be linked by way of analogy. While the linkage of classical and quantum interference may be placed on a rigorous theoretical footing, that is unnecessary for purposes of the present introduction. Suffice it to say that the expectation value of the inner product of two quantum states is analogous to the intensity detected by a square-law optical detector, and similarly sensitive to the phase of a cross-product term. Thus, interferometry, of both optical and atomic beams, is widely used for accurate measurements of various physical, chemical, and biological quantities. The basic principle of optical interferometry is that a coherent electromagnetic wave, such as a laser beam, is split into two paths, redirected, and recombined, allowing the relative phase, or optical path difference, between the two paths to be measured.

Typically, a beam splitter is used to split the laser beam into two component beams, and the two component beams are redirected using mirrors. The recombination of the laser beams is also done with a beam splitter. Optical interferometers may be used to measure the phase shift of a thin sample of a material, such as glass, or any other phenomenon that may cause a differential shift in phase in the path of a first component beam with respect to the path of a second component beam. For instance, a sample may be placed in a path of a laser beam, such as path "A" or "B" as discussed below in reference to FIG. 1, and the phase shift of the sample alters the phase relationships between the two laser beams. Optical interferometers may be used to measure surfaces, displacements, and absolute lengths. In any of these cases, the desired information is the surface or position of object(s). The desired information about the object is encoded in the reflected light and the interference of the two coherent light beams results in a change of intensity as a function of the controlled phase. This intensity variation is referred to as an interference fringe pattern or "fringes." Fringes are analyzed and are measured. Thus, interferometers can be used to measure very small displacements by using the wave property of light. This is accomplished by measuring changes of the interference pattern, i.e., "fringes," when waves with different phases overlap.

Figure 1:
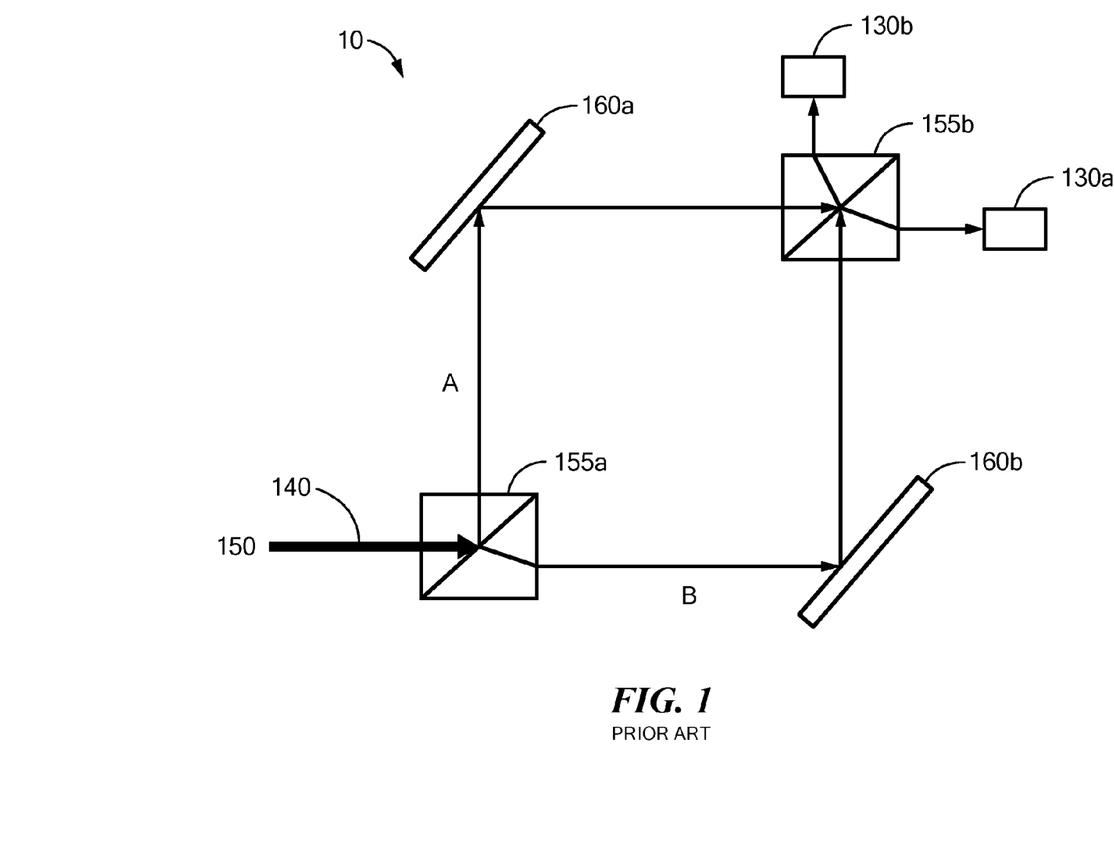
FIG. 1 is block diagram of a prior art Mach-Zehnder optical interferometer, shown and described herein by way of analogy and discussed for heuristic purposes.

Of the many optical configurations giving rise to interference effects, an example of a Mach-Zehnder type of optical interferometer is described with reference to FIG. 1 where it is designated generally by numeral 10, and includes a coherent source 150, such as a laser source, and two beam splitters 155a and 155b, two mirrors 160a and 160b, and two detectors 130a and 130b. Light entering the first detector 130a starts from the coherent source 150, which directs a laser beam 140 into the first beam splitter 155a, where it splits into a first path "A" and a second path "B." For path "A" the laser beam is reflected by the front of the first beam splitter 155a, which gives a phase change of one-half of a wavelength, and then reflects off of mirror 160a, which gives a further phase change of one-half a wavelength, and then is transmitted through the second beam splitter 155b, which results in a constant phase change. For the second path "B" the laser beam is transmitted through the first beam splitter 155a, which results in a constant phase change, and then reflects off the second mirror 160b, which results in a phase change of one-half a wavelength. Path "B" is then reflected by the second beam splitter 155b, which results in a phase change of one-half a wavelength. Light entering the first detector 130a via the two paths "A" and "B" is in phase and results in constructive interference. For light entering the second detector 130b, the paths for "A" and "B" are similar up until the second beam splitter 155b. For instance, path "A" first transmits through the second beam splitter 155b, but is then reflected by the inner surface of the second beam splitter 155b, (resulting in no phase change) and finally transmitting through the second beam splitter 155b a second time, which results in an additional constant phase change. For path "B" the laser beam transmits through the second beam splitter, resulting in a constant phase change instead of being reflected. The total difference between the two paths "A" and "B" is that the "A" path goes through one additional phase change of one-half a wavelength. This results in complete destructive interference, and no light reaches the second detector 130b. However, when a sample is placed in the path of "A" or "B," there is no longer complete destructive interference at the second detector 130b. Measuring the relative amount of light entering the first and second detector 130a and 130b allows a calculation of the phase shift produced by the sample.

While many other configurations of optical interferometers might be cited, in which the component beams traverse separated or common paths, the description of optical interferometry in terms of a Mach-Zehnder configuration, as laid out above, will suffice for present purposes.

Atom Interferometry

Atoms are useful in measurement devices in part because their own inertial frame is almost completely decoupled from their environment. That is to say that forces acting on the atoms are well-defined. Neutral atoms can make excellent test particles for measuring gravitational fields. The internal degrees of freedom for atoms include different atomic energy level, while the external degrees of freedom include different momentum states that the atoms can occupy. Atoms are capable of operating as interferometers, as now described. To exhibit interference effects, some degree of coherence is required between interfering waves. As the term is used herein, and within the scope of the present invention, coherence need not be complete, but may also be partial. In an optical interferometer, such as the Mach-Zehnder interferometer 10 described above with reference to FIG. 1, the two coherent waves are generated by a beam splitter 155 that splits the original laser beam 140 into two paths. A material component, such as a beam splitter, splits a wave into two portions. In contrast, in an atom interferometer, the two coherent waves are the two coherent states of the atom. The two states of the atom become coherent by applying a laser pulse to the initial state of the atom. This pulse is analogous to a beam splitter in optical interferometry. In atom interferometry, the coherent waves are material waves called de Broglie waves, and the beam splitter is a laser pulse electromagnetic wave. Unlike the optical interferometer 10 of FIG. 1, which is represented in a space-space diagram, an atom interferometer is typically represented in a space-time representation, as further discussed below.

Atom interferometers in accordance with some exemplary embodiments of the present invention, including the examples discussed below with respect to FIGS. 2 and 3, rely on parallel optical beams that intersect a beam of atoms traveling at a given velocity. It is to be understood that the embodiments shown are provided solely by way of example and without limitation. Thus, for example, atomic interferometers that employ any ensemble of atoms, such as a cloud of cold atoms or a slow atomic beam, for example, are within the scope of the present invention. Typically, atomic interferometer configurations employ optical components such as mirrors, beam splitters, or cat's eye retro-reflectors to generate or otherwise implement the parallel beams.

Various different types of atom interferometers, including light-pulse atom interferometers, are based on the principle that when an atom absorbs or emits a photon, momentum must be conserved between the atom and the light field. In light-pulse atom interferometers, stimulated Raman transitions commonly provide the atom optics that coherently split, reflect, and recombine atom wavepackets. One configuration of an atom interferometer is shown in FIG. 2, which illustrates a Mach-Zehnder type of atom interferometer 100 that includes two splitting processes 104 and 108 that are separated by a light pulse process 106 that acts as a mirror. The atom sample 102 is first trapped and cooled and then launched into an interferometry sequence that includes applying the light pulse sequences 104, 106 and 108. The atomic wavepacket is initially in a quantum state (in this case, a ground state) 110, and at time $t_1$, is coherently split into a superposition of two different states, ground state 112 and excited state 118, by a first Raman pi/2 pulse beam 104, which is applied in a first direction to act as an atom "splitter." Ground state 112 may also be represented herein as |g>, and excited state 118 may also be represented herein as |e>.

Each atom acts as a quantum object with its levels representing two bound eigenstates |g> and |e>. Any pure state of the atom may be represented as a vector on a Block sphere that is a superposition of basis vectors |g> and |e>. A pi pulse inverts the system. A Raman pi pulse beam 106 is then applied at time $t_2$ to act as an atom "mirror" and is placed in the center for the purposes of closing the two paths. At time $t_3$ a second Raman pi/2 pulse 108 is applied in the opposite direction as 104 to cause interference between the atoms in different states 120 and 114. Detection outputs 130a and 130b provide the measurement of interference.

Figure 2:
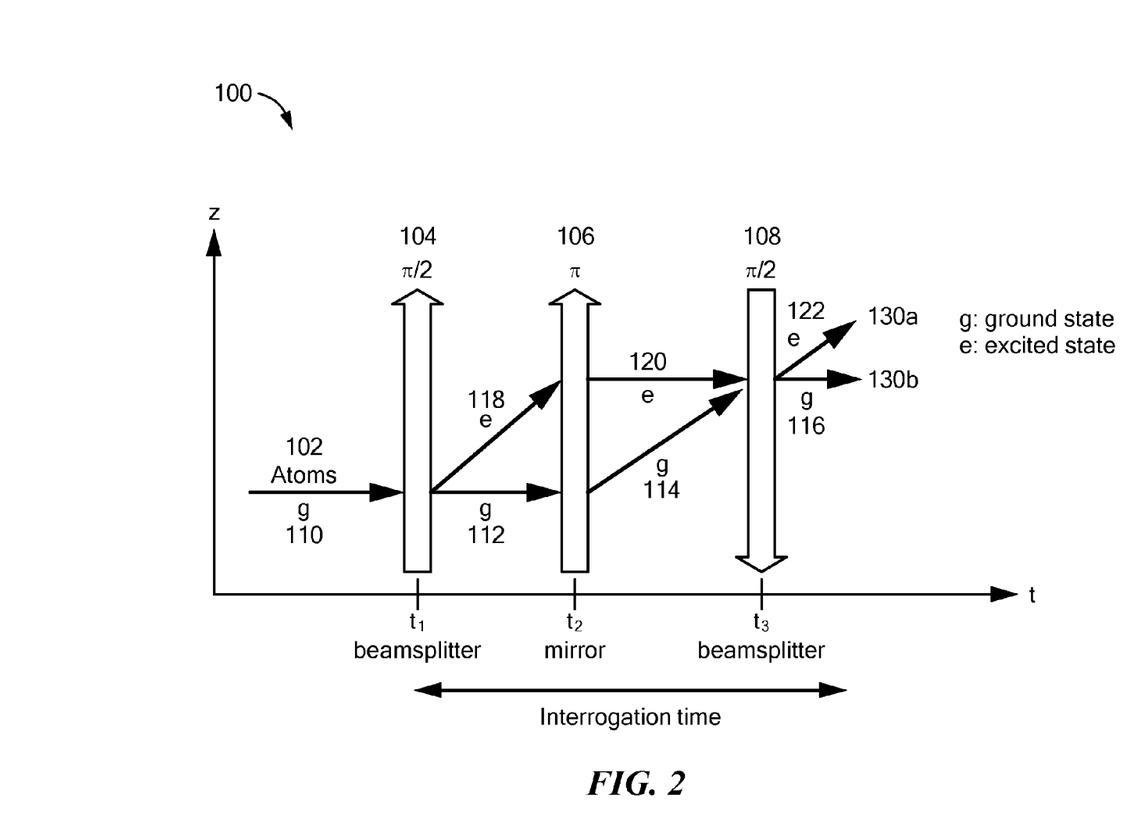
FIG. 2 is a block diagram of a Mach-Zehnder type of atom interferometer in accordance with aspects of the invention.
Figure 3:
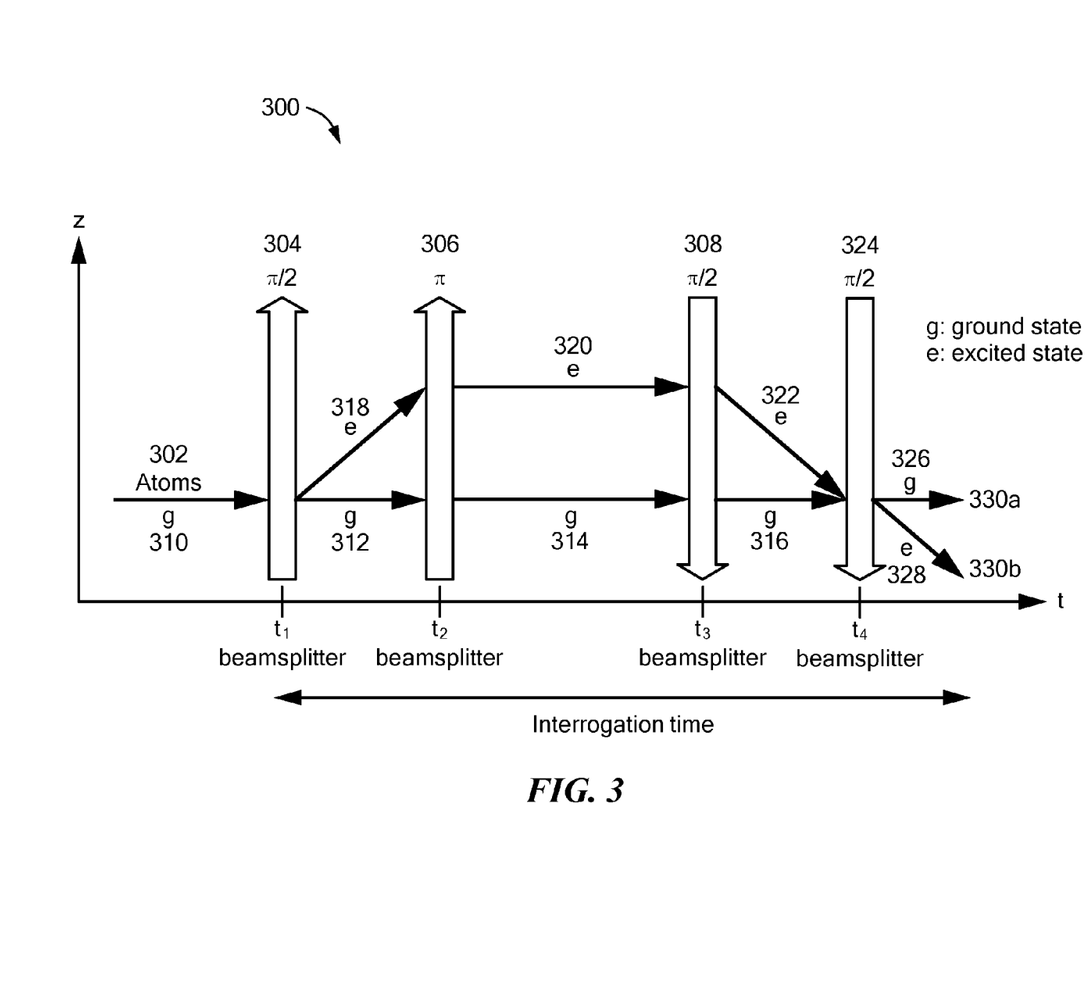
FIG. 3 is a block diagram of a Ramsey-Bordé type of atom interferometer in accordance with aspects of the invention.

In the Mach-Zehnder interferometer 100 shown in FIG. 2, the first pi/2 pulse 104 serves as the matter-wave beam splitter: the part of the atom in internal quantum state 118 traverses a different spatial path than the part in internal quantum state 112 as a result of the correlation of the atom's velocity (momentum) with its internal state. The pi pulse 106 serves in a fashion analogous to that of the mirror: it "reflects" each part of the atom so that the two trajectories will again overlap. The final pi/2 pulse 108 recombines each half of the atom so that the matter waves subsequently interfere.

Another configuration of an atom interferometer is now described with reference to FIG. 3, which illustrates a Ramsey-Bordé type of interferometer designated generally by numeral 300. The Ramsey-Bordé type of interferometer 300 uses light pulses to manipulate atoms, but includes four Raman pi/2 pulses 304, 306, 308, and 324, where light pulses 304 and 306 are directed in a first direction, and light pulses 308 and 324 are directed in an opposite direction to that of light pulses 304 and 306.

For convenience of expression, light pulses 304, 306, 308 and 324 may be referred to herein as "laser beams," in that laser beams impart the specified light pulses, and, additionally, as "beam splitters," since that is the function that they serve.

Returning to FIG. 3, atoms 302 are first split at time $t_1$ by the beam splitter 304 into two wavepackets of which 50% of the atoms remain in the ground state (312) and the other 50% go to the excited state (318) by absorbing a photon from the laser beam. At time $t_2$, the second beam splitter 306 is used to split the two wavepackets again. Two subsequent splittings are made by light pulses 308 and 324 that travel in opposite directions to the direction of light pulses 304 and 306.

As noted above in reference to the examples shown in FIGS. 2 and 3, atom interferometers are constructed to include optical beam and atom interactions that alter the population distribution between ground and excited states, where the momenta of the two states (i.e., the partial wavepackets) differ by the absorbed photon recoil. Subsequent optical beam and atom interactions cause the partial wavepackets to overlap again to create a fringe pattern. An atom interferometer can thus be created by adjusting specific parameters of the optical beams so 5 as to function as either a beam splitter (e.g., 104, 108 in FIG. 2; 304, 306, 308, 324 in FIG. 3) or mirror (e.g., 106 in FIG. 2), by imparting either a pi/2 or pi phase shift on the atom stream. The phase of the wavepacket interacting with the optical beam is shifted by the value of the instantaneous phase of the electric field $E(r,t)$ of the optical beam. The instantaneous phase shift of the interference pattern is dependent on the total phase shift imparted by all interacting optical beams.

As noted above, we have described atom interferometers in terms of space-time representations. However, the invention does not pertain to atom interferometers comprising a single laser beam or overlapping beam pair, applied to an atomic sample that is substantially stationary. The invention pertains to the types of atom interferometers shown in FIGS. 2 and 3 that employ multiple, spatially separated parallel laser beams 104, 108 (shown in FIG. 2) and 304, 306, 308, 324 (shown in FIG. 3) for producing a specified interferometer interaction. Atoms are presumed to move through these multiple laser beams, and temporal optical pulses are realized either by the atom movement through a steady state laser beam, or by laser power switching to produce an optical pulse while the atoms lie within a given atom beam.

A high degree of parallelism is critical to the operation of the sensors that are based on separated beam atom interferometry. The loss of parallelism can result in sensor drift or in certain instances, a complete loss of signal. Certain environmental influences can adversely affect beam alignment, such as temperature fluctuations, vibrations, mechanical movements, and other perturbations, making it difficult to operate these types of interferometers in dynamic environments such as these. The reader is reminded, however, that the scope of the present invention is not limited to the embodiments of FIGS. 2 and 3, and that the invention may be advantageously applied to various types of atomic interferometers employing a variety of ensembles of free atoms.

Figure 4A:
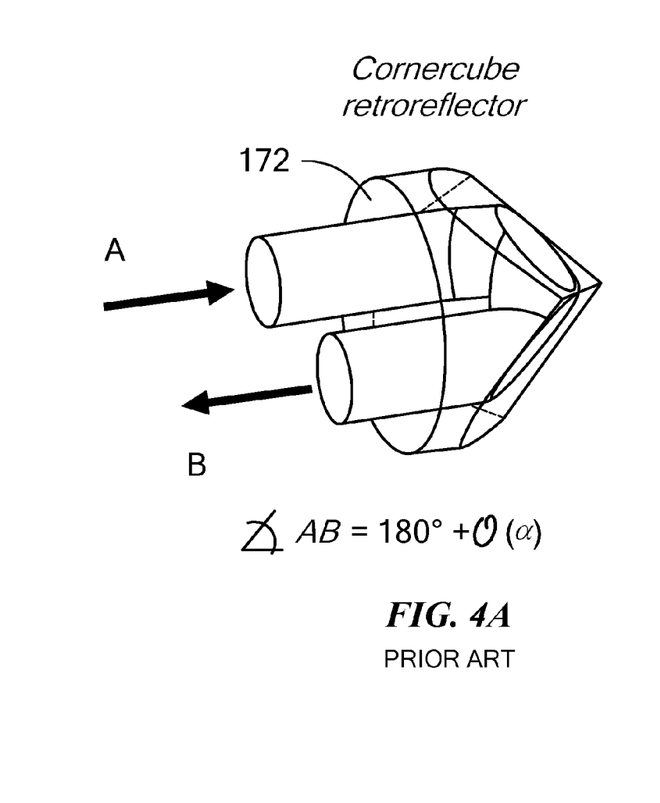
FIGS. 4A and 4B are schematic illustrations of two examples of prior art alignment-insensitive beam routing optical elements.
Figure 4B:
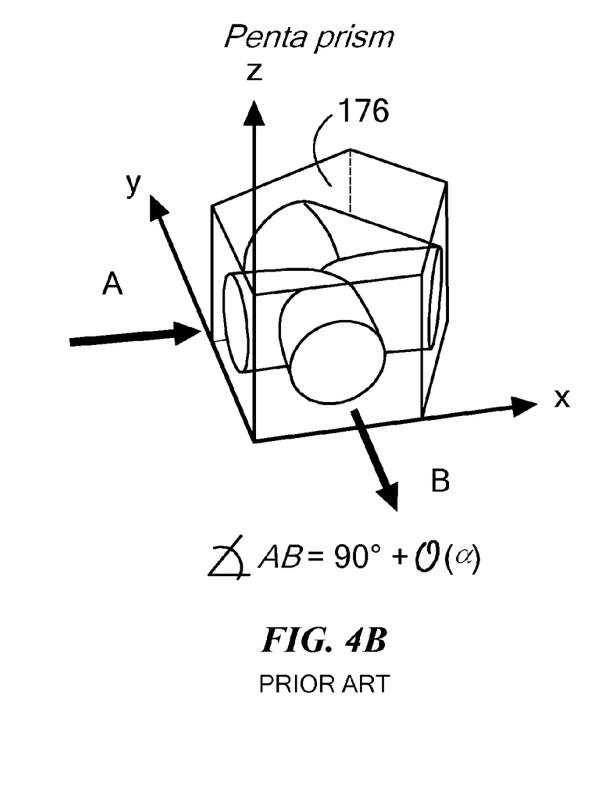

In accordance with certain embodiments of the present invention, an atom interferometer may include one or more alignment-insensitive beam routing elements, as the term is defined above. FIGS. 4A and 4B illustrate two non-limiting examples of alignment-insensitive beam routing elements, corner cube reflector 172 and monolithically mounted matched pairs of pentaprisms or pentamirrors 176. As the term is used herein, a "cornercube" shall denote a retroreflector formed by three mutually perpendicular reflecting surfaces. As used herein, the term "alignment-insensitive routing element" refers to an optical device or system where reflection is insensitive to incident angle, where "insensitive" is defined in the definition section above. For instance, FIG. 4A is an example of a cornercube retro-reflector 172 that operates under the principle of total internal reflection (TIR), where an incident beam A is reflected parallel to itself, emerging as exiting beam B (otherwise referred to herein as the "reflection") by three roof surfaces (i.e., three internal reflections). The reflection is insensitive to the incident angle, such that when the incident beam "A" enters the prism off the normal axis, the reflection B still maintains a 180 degree orientation to order a, where a is the tolerance specified in the definition of "insensitive" provided above.

Figure 5A:
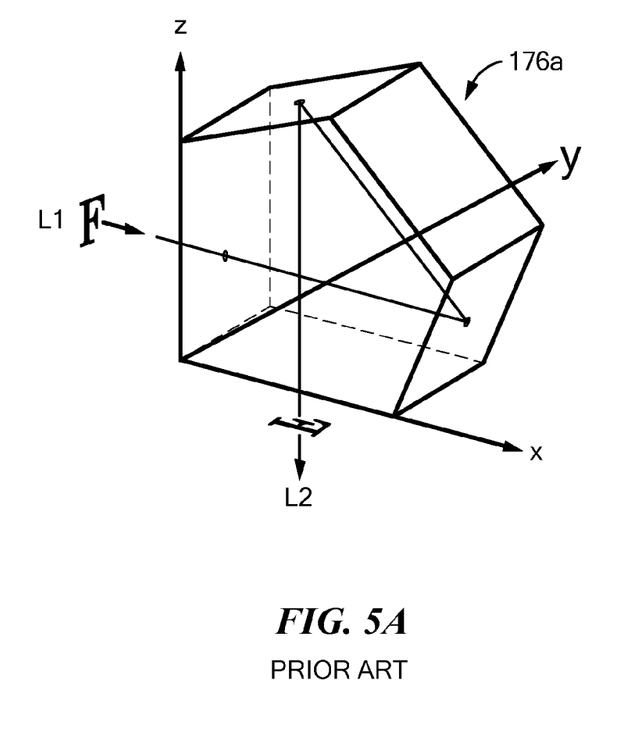
FIGS. 5A and 5B are schematic illustrations of two examples of prior art pentaprisms.
Figure 5B:
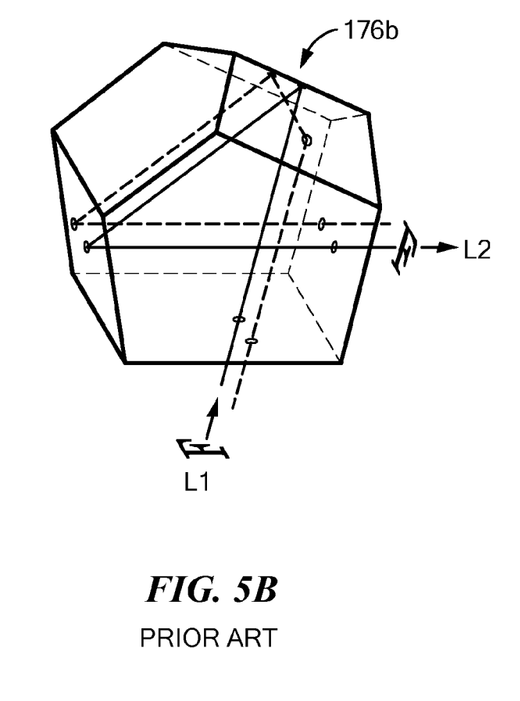

FIG. 4B is an example of a pentaprism, which is a five-sided prism that deviates the incident beam "A" by 90 degrees. Pentaprisms have been employed to achieve 90-degree reflection at least since the 1890s, when they were used in binoculars manufactured by the Hensoldt firm. FIGS. 5A and 5B illustrate two examples of pentaprisms 176a and 176b that may be implemented in systems and methods according to one or more aspects of the invention. Generally speaking, a pentaprism is a five-sided reflecting prism used to deviate a beam of light by a constant 90°. For example, an incoming beam of light (L1) enters one face of the pentaprism 170a, 170b, and reflects inside the prism twice, and exits the prism by a constant 90° (L2). The beam of light is deviated by a constant 90°, even if the entry beam is not at 90° to the prism. FIG. 5B is an example of a roof pentaprism, and includes two sloping sides on one of the reflecting surfaces (such as on top surface 177, as shown in FIG. 5B). In certain instances, one or more of the reflecting faces of the pentaprism may be coated with a reflective coating, such as aluminum, silver, gold, etc. Matched pairs of pentaprisms and pentamirrors are advantageously employed to substantially cancel errors in the manufacturing of individual components.

Figure 6A:
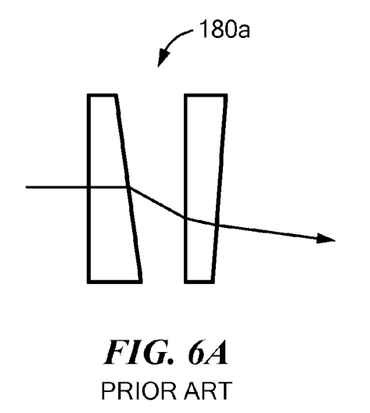
FIGS. 6A-6D are schematic illustrations of three orientations of prior art prism pairs.
Figure 6B:
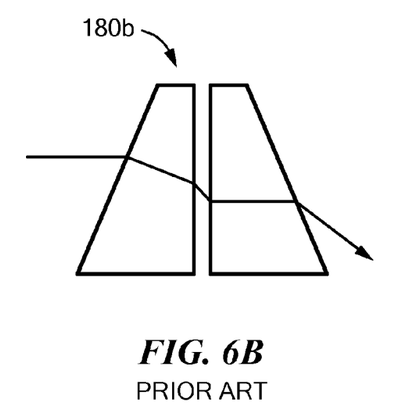
Figure 6C:
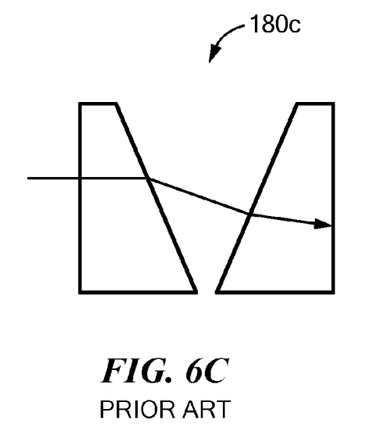
Figure 6D:
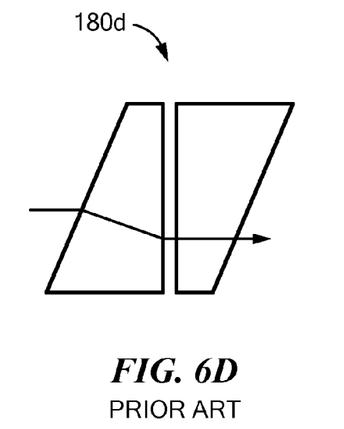

According to at least one embodiment, an atom interferometer may include one or more refractive beam deflection elements, each of which may also be referred to herein as a refractive beam steering element. As used herein, the term "refractive beam deflection element" refers to an optical device or system that is configured to redirect a beam that is incident normal to the incident surface of the optical device or system using refractive properties of the element in contradistinction to reflection. In certain instances, the beam deflection element is configured to reduce sensitivity to tilt. FIGS. 6A-6D illustrate examples of refractive beam deflection elements 180a-180d, which, in this example, are each a pair of wedge prisms, such as a Risley prism pair, first described by Samuel Doty Risley in Risley, "*A New Rotary Prism,*" *Trans. Am. J. Opthalmol.*, vol. 5, pp. 412-13 (1889) (cited in Carter, "*Risley Prisms: 125 Years of New Applications,*" *Eos*, vol. 87, pp. 273-276, (2006)). The slant faces of wedge prisms 180a of FIG. 6A are arranged in a "face-to-back" configuration. The slant faces of wedge pair 180b of FIG. 6B are arranged in a "back-to-back" configuration, where the slant faces are disposed outwardly, and in FIG. 6C the slant faces of wedge pair 180c are arranged in a "face-to-face" configuration, where the slant faces are disposed inwardly. The slant faces of wedge pair 180d also face outwardly, but one wedge of the pair is also rotated 180 degrees vertically. In each of the beam deflection elements 180a-180d, beam steering is accomplished by rotating one wedge in relation to the other, which changes the direction of the beam. When the wedge prisms are oriented in the "back-to-back" configuration as shown in FIG. 6B, both prisms refract light in the same direction and act as a single prism with twice the prism angle of either, which allows for maximum beam deflection. In contrast, the configuration in FIG. 6D allows for minimum beam deflection.

Figure 7A:
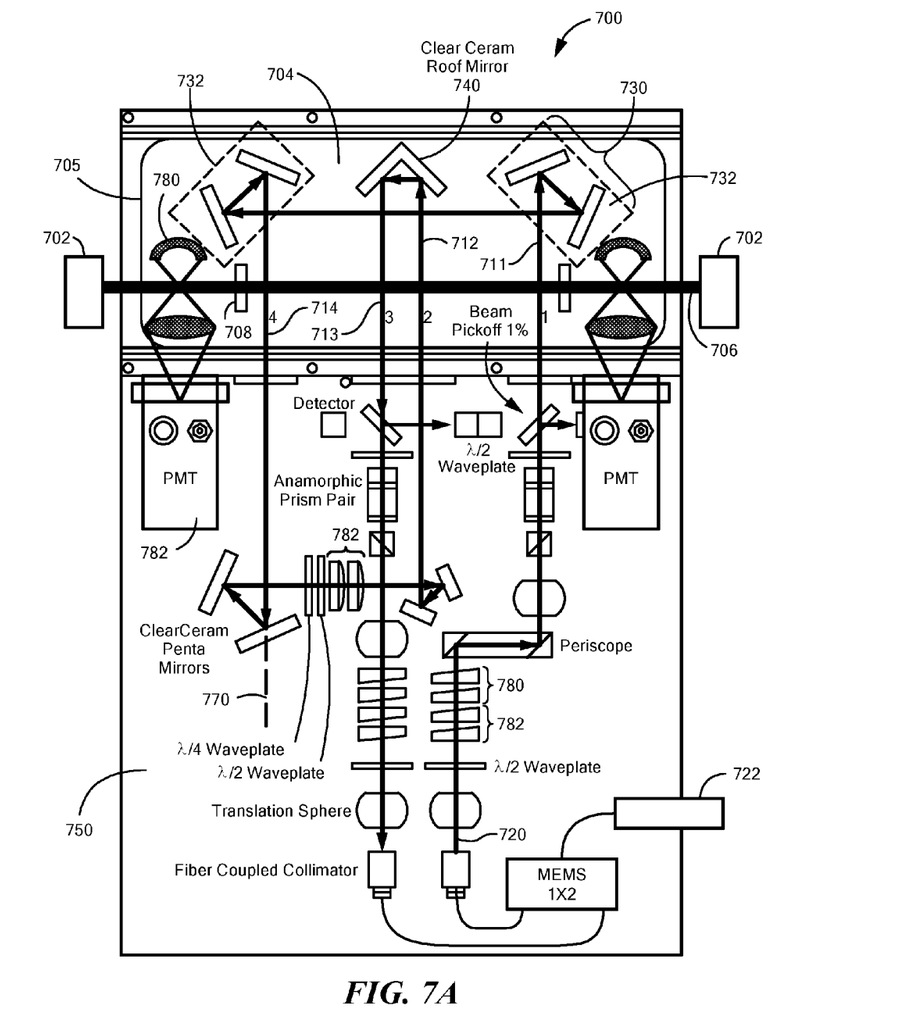
FIGS. 7A-7C are top view schematic illustrations of embodiments of a Ramsey atomic interferometer implemented with at least one alignment-insensitive beam routing element in accordance with an aspect of the present invention.
Figure 7B:
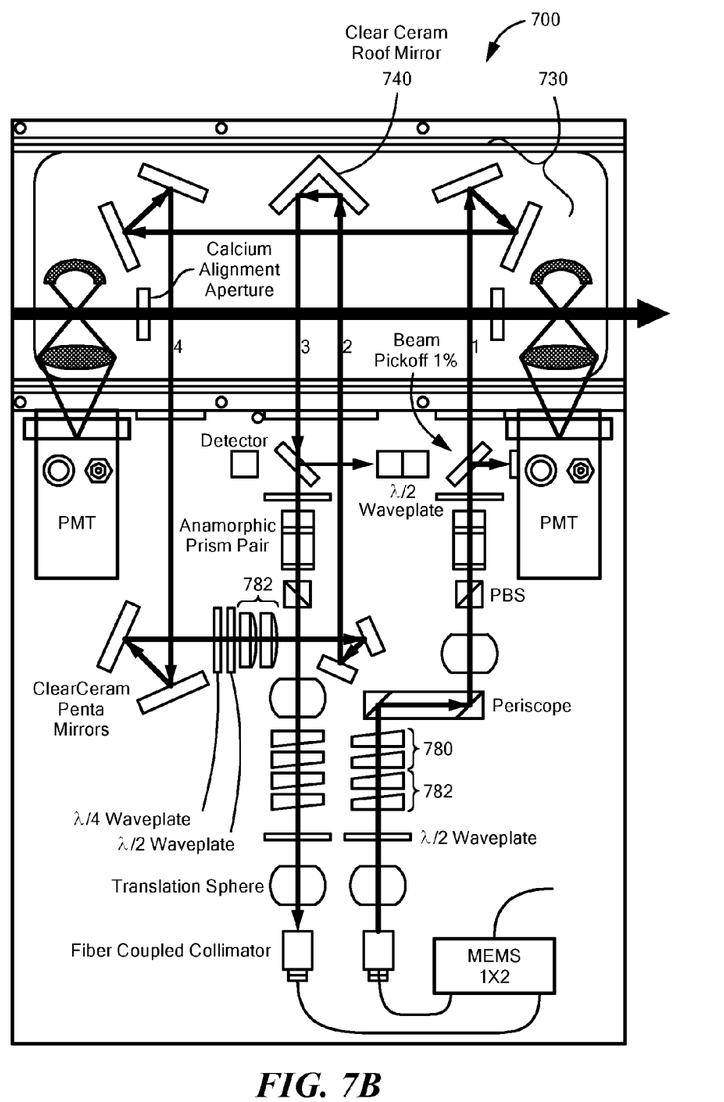
Figure 7C:
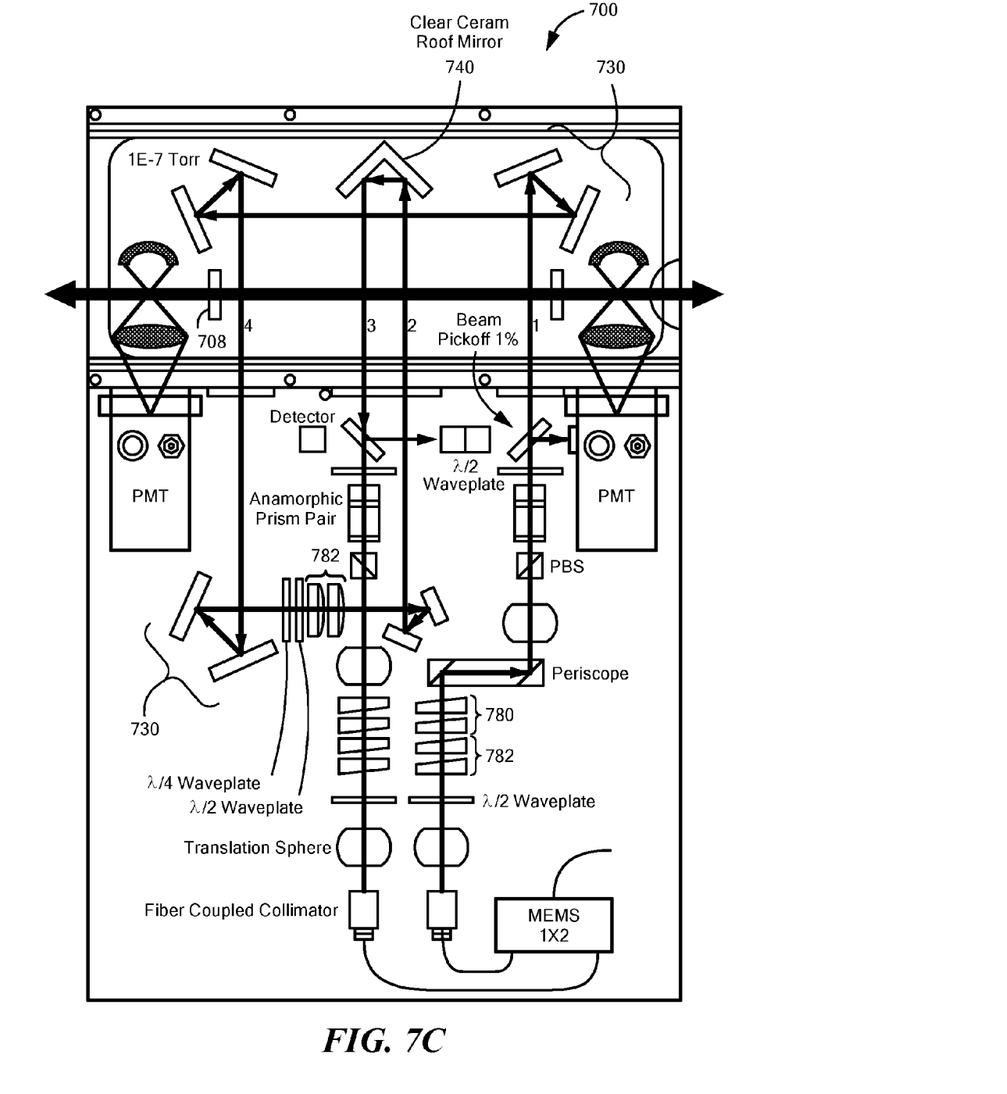

FIGS. 7A-7C are each top view schematics of an example of a 4-beam Ramsey-Bordé optical reference apparatus 700 that may be implemented in accordance with one or more aspects of the invention. It is to be understood that whether the apparatus is used as a frequency reference, or for any other purpose, atomic interferometers as described herein are within the scope of the presently claimed invention, and may be referred to herein simply as "apparatus" 700.

As shown in FIGS. 7A-7C, the apparatus 700 may include two identical atom beam sources 702 placed at one or both opposite ends of an evacuated vessel 704, otherwise referred to herein as a "vacuum enclosure" or a "vacuum chamber." It is to be noted that slow atomic beams, as well as clouds of cold atoms, are encompassed within the meaning of ensembles of free atoms as used herein, and are within the scope of the present invention. Corresponding sources are employed for generating an ensemble of atoms within vacuum enclosure 704. Where the free atoms comprise a thermal atomic beam, atom source 702 is a thermal atomic beams source, and may be referred to as such herein without limitation.

The pressure in vacuum enclosure 704 is typically on the order of ~$10^{-7}$ Torr. Vacuum enclosure 704 is bounded by vacuum chamber wall 705. Each thermal atom beam source 702 emits a thermal atom beam 706 of atoms, such as Ca, for example, named here solely by way of example and without limitation. The thermal atomic beam(s) 706 may be configured oppositely directed (as shown in FIG. 7C) and configured to pass through parallel laser beams. The thermal atomic beam(s) may be configured to be directed in a single direction (as shown, for example, in FIG. 7A, or dual directions (opposing directions) (as shown, for example, in FIG. 7C). Alignment of atomic beam 706 is provided by alignment aperture 708.

According to at least one embodiment of the present invention, atom beam 706 is laser cooled. In some embodiments, the atom beam is comprised of one or more laser cooled atom clouds. For instance, the atom beam may be comprised of a series of laser cooled atom clouds.

As shown in FIGS. 7A-7C, the thermal atomic beams 706 are configured to pass through two or more parallel laser beams. The term "parallel" as used herein, encompasses beams whose Poynting vectors are either parallel or antiparallel. For example, FIGS. 7A-7B show an atomic beam 706 that passes through four parallel laser beams 711, 712, 713, and 714. As shown in FIGS. 7A-7C, the four laser beams 711, 712, 713, and 714 are generated from a single input beam 720 generated by a substantially coherent source 722, which may be tunable, within the scope of the present invention. Input beam 720 may be redirected through a sequence of a monolithically-mounted matched pair of pentamirrors 730 and/or one or more retroreflectors 740 that are positioned inside and/or outside the vacuum enclosure 704 containing the atomic beams 706. Pentaprisms may similarly be employed within the scope of the present invention. The monolithically-mounted pair of pentamirrors or pentaprisms are selected so that any excursion from perfect orthogonality of incident and emergent beams due to fabrication is nearly identical in each pentaprism of the pair. Thus, when matched pairs of pentamirrors or pentaprisms are mounted in opposing orientation, the excursion is canceled. Pentamirrors 730 are mounted in pairs by bonding directly to a base 732 so as to form a monolithic structure that allows no differential movement of one pentaprism with respect to another. Bonding of pentamirrors 730 to base 732 is preferably optical bonding.

The optical train is preferably configured, as shown in FIGS. 7A-7C, such that any perturbations to the direction of beams 711 and 714 are common-mode to the two beams, and that, similarly, that any perturbations to the direction of beams 712 and 713 are common-mode to those two beams. All alignment is accomplished by means of one or more entirely refractive optics, such as coarse alignment Risley prism pair 780 and fine alignment Risley prism pair 782, thereby advantageously removing any mechanical tolerances from the alignment-insensitive optical elements desensitizing alignment.

By virtue of the teachings of the present invention, any excursion from parallelism of a second beam path of two anti-parallel beam paths with respect to the first beam path of the two anti-parallel beam paths that is within the aperture of the respective pentamirror pairs 730 is rigorously canceled, and independent of variation of the first laser beam path with respect to excursions in yaw parallel to the underlying plane. To the knowledge of the inventors, this has never been capable of achievement using any known means of traversing an atomic beam with a pair of antiparallel optical beams. Atoms of atomic beam 706 that have traversed four parallel laser beams 711, 712, 713, and 714, insofar as they remain in excited state |e>, will fluoresce, and their spontaneous fluorescence will be directed by collection optics 780 onto detector 782, typically a photomultiplier.

Additionally, the apparatus 700 may include optics configured for generating sets of laser beams that propagate in opposite directions. The optics serving that indicated purpose may be referred to herein collectively as an "optical components train." In some embodiments, the input laser beam 720 comprises a single optical frequency that can be controlled by controlling source 722. The light source 722 may comprise at least one frequency tunable laser configured to produce a laser beam, which is in turn redirected through the vacuum chamber 704 to produce one or more laser beams 711, 712, 713, and 714, as exemplified in FIGS. 7A-7C, each of which includes four laser beams.

In accordance with some embodiments, including at least one embodiment directed to a Ramsey-Bordé interferometer, the two oppositely directed atomic beams 711, 714 are continuously generated, and a single set of four laser beams is applied at a time to the atom beams, with periodic change in direction of the applied laser beams.

In various embodiments, a base plate 750 supporting one or more of the pentaprisms 730 and/or retroreflectors 740 may be made of aluminum, stainless steel, Zerodur®, or Clearceram®. Base plate 750 may also be referred to herein as a mounting base plate 750, insofar as optical components are mounted thereto. In some embodiments, including one embodiment directed to a Ramsey-Bordé interferometer, the mounting baseplate 750 of the optical components train generating the four laser beams 711, 712, 713, and 714 also serves as one wall (bottom) of the vacuum enclosure 704. This configuration may improve control of the relative position of the optical components with respect to the atom sources 702. This configuration may also allow for atom beam collimation slits 708 to be directly supported by the base plate 750, so as to better control relative location of the optics and the atom beam.

The plane most nearly coincident with an upper surface of base plate 750 shall be referred to herein as an "underlying plane."

According to some embodiments, including at least one embodiment directed to a Ramsey-Bordé interferometer, a portion of the optical components train generating four laser beams resides within the vacuum region 704. According to an alternative embodiment, the optical components may be positioned outside the vacuum region 704.

The entire optical reference apparatus 700 may be enclosed in one or more layers of material that serve as a magnetic shield and/or thermal isolator. According to some embodiments, the enclosure also includes one or more layers of insulation that are positioned in between the layers 10 that comprise the magnetic shield and/or thermal isolator. The enclosure may also include one or more openings for optical fibers and electrical cables to be introduced into the apparatus 700. The enclosure may be comprised in full or in parts of one or more layers of material with a high-p value (where p refers to the permeability of a material to magnetic fields) such as MUMETAL®, HIPERNOM®, and PERMALLOY®.

According to some embodiments, the apparatus may also comprise a vibration isolation platform (not shown).

According to various aspects, the optical elements may be implemented into multiple atom interferometers. For instance, a first atom interferometer comprising a first thermal atomic beam and a second atom interferometer may comprises a second thermal atomic beam. The optical elements may be using in one or more of the light paths implemented into the first and second atom interferometer, as described above. According to some embodiments, at least one frequency-tunable laser light source may be configured to apply laser light to the first atomic beam and the second thermal atomic beam. In some embodiments, the first and second atom interferometer share at least one light source. In other embodiments, the first and second atom interferometers have independent light sources.

In accordance with certain embodiments, one or more of the optical elements discussed herein may be implemented into an atom interferometer configured for inertial sensing or atomic time-keeping. As such, beam splitter and/or mirror sequences may be applied to a cloud of atoms and measurements may be used to generate a signal. The signal may be used to control one or more operations in a navigation device or system, for example, in operations related to determining location. For instance, measurements related to acceleration or rotation sensing may be used to generate a control signal that is then used by a navigation device. In alternative embodiments, the signal is a clock signal that may be used in applications directed to atomic time-keeping.

The aspects disclosed herein in accordance with the present invention, are not limited in their application to the details of construction and the arrangement of components set forth in the following description or illustrated in the accompanying drawings. These aspects are capable of assuming other embodiments and of being practiced or of being carried out in various ways. Examples of specific implementations are provided herein for illustrative purposes only and are not intended to be limiting. In particular, acts, components, elements, and features discussed in connection with any one or more embodiments are not intended to be excluded from a similar role in any other embodiments.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated reference is supplementary to that of this document; for irreconcilable inconsistencies, the term usage in this document controls. Moreover, titles or subtitles may be used in the specification for the convenience of a reader, which shall have no influence on the scope of the present invention.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

The embodiments of the invention described herein are intended to be merely exemplary; variations and modifications will be apparent to those skilled in the art. All such variations and modifications are intended to be within the scope of the present invention as defined in any claims appended to any application claiming priority herefrom.

We claim:
1. An atomic interferometer comprising:
   a. an ensemble of atoms;
   b. a laser beam traversing the ensemble of atoms in a first laser beam path;
   c. an optical components train, comprising at least one alignment-insensitive beam routing element, configured to reflect the laser beam along a second laser beam path that is anti-parallel with respect to the first laser beam path;

d. an entirely refractive alignment element for steering the laser beam into the optical components train; and a detector configured to detect spontaneous fluorescence emitted by atoms within the ensemble of atoms after traversal of the first and second laser beam paths.

2. An atomic interferometer in accordance with claim 1, wherein the ensemble of atoms includes a beam of atoms traversing a vacuum chamber.

3. An atomic interferometer in accordance with claim 1, wherein the alignment-insensitive beam routing element includes at least one of a pentaprism pair, a pentamirror pair, a roof pentaprism pair, a roof pentamirror pair, a corner cube and a roof reflector.

4. An atomic interferometer in accordance with claim 2, wherein the alignment-insensitive beam routing element is disposed within the vacuum chamber.

5. An atomic interferometer in accordance with claim 2, wherein any angular perturbation of the first laser beam path external to the vacuum chamber is common to the first laser beam path and the second laser beam path.

6. An atomic interferometer comprising:
 a. an ensemble of atoms
 b. a laser beam traversing the ensemble of atoms;
 c. an optical component train, comprising at least one alignment-insensitive beam routing element, configured within the vacuum enclosure to reflect the laser beam along a second laser beam path that is anti-parallel with respect to the first laser beam path;
 d. an entirely refractive alignment element for steering the laser beam into the optical components train; and
 e. a detector configured to detect spontaneous fluorescence emitted by atoms within the beam of atoms after traversal of the first and second laser beam paths,
  wherein any excursion in yaw of the first laser beam path with respect to the ensemble of atoms is rigorously common mode to the first and second laser beam paths.

7. An atomic interferometer in accordance with claim 6, wherein the alignment-insensitive beam routing element includes at least one of a monolithically mounted pentaprism pair, a monolithically mounted pentamirror pair, and a roof reflector.

8. An atomic interferometer in accordance with claim 7, wherein the alignment-insensitive beam routing element includes a matched pair of pentaprisms or pentamirrors.

9. An atomic interferometer in accordance with either claim 2 or claim 6, further comprising at least a second alignment-insensitive beam routing element, configured within the vacuum enclosure to reflect the laser beam along a fourth laser beam path that is anti-parallel with respect to a third laser beam path.

10. A method for measuring relative phase shifts in interference fringes between populations of internal states of a quantum system, the method comprising:
 a. generating an ensemble of free atoms within a vacuum chamber;
 b. coupling a laser beam so as to traverse the ensemble of atoms in a first laser beam path;
 c. configuring at least one alignment-insensitive beam routing element within the vacuum enclosure to reflect the laser beam along a second laser beam path that is anti-parallel with respect to the first laser beam path;
 d. aligning the first laser beam path with respect to the ensemble of atoms solely by refractive optics; and
 e. detecting spontaneous fluorescence emitted by atoms within the ensemble of atoms after traversal of the first and second laser beam paths.

11. A method in accordance with claim 10, wherein configuring the at least one alignment-insensitive beam routing element includes providing at least one of a monolithically mounted pentaprism pair, pentamirror pair and a roof reflector.

* * * * *